US012383144B2

(12) United States Patent
Vermeulen et al.

(10) Patent No.: US 12,383,144 B2
(45) Date of Patent: Aug. 12, 2025

(54) SYSTEM AND METHOD FOR PROVIDING AN INDICATION OF A PERSON'S GUM HEALTH

(71) Applicant: KONINKLIJKE PHILIPS N.V., Eindhoven (NL)

(72) Inventors: Olaf Thomas Johan Antonie Vermeulen, Oss (NL); Steven Charles Deane, Cambridge (GB); Lucas Petrus Henricus Scheffers, Utrecht (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1190 days.

(21) Appl. No.: 17/269,067

(22) PCT Filed: Aug. 15, 2019

(86) PCT No.: PCT/EP2019/071926
§ 371 (c)(1),
(2) Date: Feb. 17, 2021

(87) PCT Pub. No.: WO2020/035562
PCT Pub. Date: Feb. 20, 2020

(65) Prior Publication Data
US 2021/0315459 A1    Oct. 14, 2021

(30) Foreign Application Priority Data

Aug. 17, 2018 (EP) .................................... 18189605

(51) Int. Cl.
*A61B 5/00* (2006.01)
*A47G 19/22* (2006.01)
*A61B 10/00* (2006.01)

(52) U.S. Cl.
CPC ........ *A61B 5/0088* (2013.01); *A47G 19/2227* (2013.01); *A61B 5/0075* (2013.01);
(Continued)

(58) Field of Classification Search
CPC ... A61B 5/0075; A61B 5/0088; A61B 5/4552; A61B 5/14551; A61B 10/0051;
(Continued)

(56) References Cited

U.S. PATENT DOCUMENTS 6,029,304 A * 2/2000 Hulke ................ A46B 15/0036
15/105
6,434,172 B1 * 8/2002 DiGiovanni ............ H01S 3/302
372/102
(Continued)

FOREIGN PATENT DOCUMENTS

CN     104880391 A    2/2015
EP     2660597 A1    11/2013
(Continued)

OTHER PUBLICATIONS

Ogawa, Fundamentals of Colorimetric Analyzers, Biological Sample Analysis, 2013, 36(3), 273-280.
(Continued)

*Primary Examiner* — Charles A Marmor, II
*Assistant Examiner* — Andrew E Hoffpauir (57) ABSTRACT

An optical analysis of saliva or a fluid-saliva mix obtained during or after an oral care action is performed in order to check whether the saliva or fluid-saliva mix contains blood, which allows for determining whether or not a person may suffer from gingivitis or another condition affecting gum health. In particular, light received from a representative sample (23) containing saliva is detected and analyzed. The analysis involves determination of measurement values of light received by a light-receiving unit (25) for one or more main wavelengths of the light and one or more auxiliary wavelengths of the light. Advantageously, the main wavelength(s) is/are associated with high hemoglobin absorption and the auxiliary wavelength(s) is/are associated with low hemoglobin absorption. A measurement value at an auxiliary
(Continued)

wavelength is used for correcting a measurement value at as main wavelength for background influences.

19 Claims, 3 Drawing Sheets

(52) U.S. Cl.
CPC ........ *A61B 5/4552* (2013.01); *A61B 10/0051* (2013.01); *A47G 2019/2238* (2013.01)

(58) Field of Classification Search
CPC . A46B 15/0002; A46B 15/0036; A61C 19/04; A47G 19/2227; A47G 2019/2238; G01N 21/51; G01N 21/3151; G01N 21/314; G01N 21/4738; G01N 2021/3166; G01N 2021/3181; G01N 2021/4757; G01N 2021/4769; G01N 33/487; G01J 3/027; G01J 3/42; G01J 3/427

See application file for complete search history.

(56) References Cited

U.S. PATENT DOCUMENTS

| | | | |
|---|---|---|---|
| 6,501,460 B1* | 12/2002 | Paik | G06F 3/0317 345/166 |
| 7,386,333 B1* | 6/2008 | Birecki | A61B 5/0088 600/310 |
| 2002/0039343 A1* | 4/2002 | Shindo | G11B 7/12 369/112.29 |
| 2003/0185716 A1* | 10/2003 | Goldstein | A61L 9/03 422/124 |
| 2008/0060148 A1* | 3/2008 | Pinyayev | A61B 5/0088 15/4 |
| 2008/0276393 A1* | 11/2008 | Russell | A46B 15/0002 15/105 |
| 2008/0303411 A1* | 12/2008 | Ohta | C09K 11/02 445/35 |
| 2010/0013968 A1* | 1/2010 | Kim | H04N 23/57 348/294 |
| 2010/0231893 A1 | 9/2010 | Miller | |
| 2011/0050431 A1 | 3/2011 | Hood et al. | |
| 2011/0102768 A1 | 5/2011 | Dosmann et al. | |
| 2013/0078966 A1* | 3/2013 | Chang | H04W 76/10 455/414.1 |
| 2013/0253286 A1 | 9/2013 | Fridman | |
| 2013/0323673 A1* | 12/2013 | Hakomori | A61B 1/00009 433/29 |
| 2014/0242682 A1* | 8/2014 | Curry | G01N 33/574 435/287.2 |
| 2014/0246690 A1* | 9/2014 | Moosburger | G03B 15/05 257/98 |
| 2014/0312232 A1* | 10/2014 | Gronlund | A61B 5/0075 250/339.01 |
| 2015/0038350 A1* | 2/2015 | Nishinaga | G01N 33/5302 506/10 |
| 2015/0265193 A1 | 9/2015 | Lu et al. | |
| 2015/0297085 A1* | 10/2015 | Simons | A61C 19/04 15/22.1 |
| 2015/0338387 A1 | 11/2015 | Ehrenkranz et al. | |
| 2016/0015321 A1* | 1/2016 | Hashemian | G16H 10/40 600/349 |
| 2016/0047740 A1 | 2/2016 | Park et al. | |
| 2016/0080548 A1 | 3/2016 | Erickson et al. | |
| 2016/0270716 A1* | 9/2016 | Guan | A61B 1/000094 |
| 2017/0007215 A1 | 1/2017 | Podoly | |
| 2017/0212739 A1* | 7/2017 | Catiller | G06F 15/7889 |
| 2017/0328920 A1 | 11/2017 | Xu et al. | |
| 2019/0175104 A1* | 6/2019 | Malik | A61B 5/145 |
| 2019/0328234 A1* | 10/2019 | Seibel | A61B 5/14539 |

FOREIGN PATENT DOCUMENTS

| | | | |
|---|---|---|---|
| JP | 53106093 A | 9/1978 | |
| WO | WO-2016095606 A1 * | 6/2016 | ......... A61B 10/0051 |
| WO | 2021025661 A1 | 2/2021 | |

OTHER PUBLICATIONS

International Search Report and Written Opinion, International Application No. PCT/EP2019/071926, Mailed on Feb. 20, 2020.
Lobene, R. et al., "A modified gingival index for use in clinical trials", Clin Prev Dent. Jan.-Feb. 1986;8(1):3-6.
Hanioka T, et al., (1990) Hemoglobin concentration and oxygen saturation of clinically healthy and inflamed gingiva in human subjects. Journal of periodontal research 25: 93-98.

* cited by examiner

SYSTEM AND METHOD FOR PROVIDING AN INDICATION OF A PERSON'S GUM HEALTH

This application is the U.S. National Phase application under 35 U.S.C. § 371 of International Application No. PCT/EP2019/071926, filed on 15 Aug. 2019, which claims the benefit of European Application Serial No. 18189605.1, filed 17 Aug. 2018. These applications are hereby incorporated by reference herein.

FIELD OF THE INVENTION

The invention relates to a system configured to provide an indication of a person's gum health, and also relates to a method of providing an indication of a person's gum health.

BACKGROUND OF THE INVENTION

In the field of oral healthcare, hygiene and health of teeth and gums are of utmost importance. In order to ensure an optimal level of hygiene and health of teeth and gums, regular inspection of various oral conditions is needed. One of the common problems that may occur and that may go unnoticed if no specific inspection is done is gingivitis.

Gingivitis is inflammation of the gums, characterized by swollen gums, oedema and redness. The primary cause of gingivitis is plaque build-up, mostly in the gingival sulcus (pockets). Gingivitis most often occurs in hard to reach areas, such as interproximal areas, i.e. areas between adjacent teeth, and around the posterior teeth, which are difficult to clean properly.

Gingivitis can be reversed by improved oral hygiene, especially in an early stage of the inflammation. As gingivitis can propagate to irreversible periodontitis, it is important to maintain a high level of oral health and to detect gingivitis as soon as possible.

It is known to visually diagnose gingivitis by assessing reddening and swelling of the gingiva. For example, it is known to use a non-contact gingivitis index. However, this way of doing has limited sensitivity and is highly dependent on the color rendering index of the light source that is used in the process, e.g. modern phosphor converted LEDs can have a low CRI (Color Rendering Index) resulting in poor visual judgements. In general, self-diagnosis of gingivitis is difficult, all the more since gingivitis often occurs at the back of the mouth, as mentioned earlier.

Another known method for assessing whether a person suffers from gingivitis involves the use of a probe for investigating tissue areas in a person's mouth and enabling detection of gingivitis on the basis of DRS (Diffuse Reflective Spectroscopy). Applying DRS techniques offers the possibility to determine increased total hemoglobin concentration and decreased blood oxygenation related to gingivitis. Although DRS enables a sensitive method of detecting moderate gingivitis, it has some disadvantages, which reside in the facts that accurate positioning of the probe is required, that it is sensitive to movements, and that the measurement can be corrupted when blood is pushed away from the tissue under investigation when direct contact between the probe and the tissue takes place at too high force.

It is an object of the invention to fulfill the need for easy and reliable detection of moderate gingivitis. To put it more generally, it is an object of the invention to fulfill the need for easy and reliable assessment of gum health. Preferably, the detection should be of such nature that it can easily be combined with normal/daily oral hygiene routines such as brushing and flossing.

SUMMARY OF THE INVENTION

According to the invention, a method of providing an indication of a person's gum health is based on an evaluation of the presence of blood traces in a sample containing the person's saliva,
   wherein light is emitted to a sample containing the person's saliva, received back from the sample and analyzed,
   wherein measurement values of the light received back from the sample are determined for one or more main wavelengths of the light related to higher light absorption by a constituent of blood, and also for one or more auxiliary wavelengths of the light related to lower light absorption by a constituent of blood, and
   wherein a discrimination value is determined on the basis of the measurement values, wherein in the process of determining the discrimination value, a measurement value relating to a main wavelength is adjusted with (a) measurement value(s) relating to one or more auxiliary wavelengths so as to correct the measurement value relating to the main wavelength for background influences.

Accordingly, the invention provides a system that (i) is configured to provide an indication of a person's gum health on the basis of an evaluation of the presence of blood traces in a sample containing the person's saliva and (ii) comprises a light-emitting unit configured to emit light to a sample containing saliva, a light-receiving unit configured to receive light back from the sample, and an analysis unit configured to perform an analysis of light received by the light-receiving unit and to provide output representative of a person's gum health, and configured to execute at least one algorithm according to which
   measurement values of light received by the light-receiving unit are determined for one or more main wavelengths of the light related to higher light absorption by a constituent of blood, and also for one or more auxiliary wavelengths of the light related to lower light absorption by a constituent of blood, and
   a discrimination value is determined on the basis of the measurement values, wherein in the process of determining the discrimination value, a measurement value relating to a main wavelength is adjusted with (a) measurement value(s) relating to one or more auxiliary wavelengths so as to correct the measurement value relating to the main wavelength for background influences.

It is estimated that 50% to 70% of adults have gingivitis, but until the inflammation has become so severe that their gums bleed heavily during brushing, they are unaware of it. In the early stages of gingivitis, the gums bleed as well during brushing, but the amount of blood loss is so low that it is not noticeable with the naked eye in saliva or a fluid-saliva mix such as a toothpaste-saliva mix. When colored toothpaste is used, noticing blood loss becomes even more difficult, especially when the toothpaste is red. The invention is based on an insight that it is possible to diagnose gingivitis on the basis of measurements aimed at determining whether or not blood is present in saliva or a fluid-saliva mix as a result of an oral care action such as brushing or flossing. In the context of the invention, a sensitive method has been developed by means of which it is possible to trace even very small quantities of blood in saliva or a fluid-saliva mix, so that gingivitis may be diagnosed in an early stage.

When the invention is put to practice, an optical analysis of saliva or a fluid-saliva mix is performed in order to check whether the saliva or fluid-saliva mix contains blood. In particular, light received from a representative sample containing saliva is detected and analyzed, which light is obtained by emitting light to the sample and receiving the light back from the sample. The analysis is done in a particular way and comprises the steps as defined in the foregoing. Advantageously, investigating a representative sample is done during or after an oral care action is performed in the person's mouth.

A first step involves determination of measurement values of light received by the light-receiving unit for one or more main wavelengths of the light, and also for one or more auxiliary wavelengths of the light. The measurement values may be transmission values, for example. According to the invention, the measurement values are determined for a limited number of wavelengths of the light only, namely one or more main wavelengths and one or more auxiliary wavelengths, wherein it may be sufficient to have one or two main wavelengths and one or two auxiliary wavelengths, although a higher number of main wavelengths and auxiliary wavelengths is covered by the invention as well.

A second step involves determination of a discrimination value on the basis of the measurement values, wherein in the process of determining the discrimination value, a measurement value relating to a main wavelength is adjusted with (a) measurement value(s) relating to one or more auxiliary wavelengths. In case measurement values relating to two or more main wavelengths are used for the purpose of determining a discrimination value, each of those measurement values may be adjusted with (a) measurement value(s) relating to one or more auxiliary wavelengths. In such a case, the analysis unit may be configured to calculate a discrimination value that is a combination of the adjusted measurement values of the main wavelengths, such as a weighed sum of the adjusted measurement values of the main wavelengths.

In a general sense, the discrimination value may be regarded as being representative of information that is related to a person's gum health in some way, and as being suitable to be used for the purpose of determining output representative of the person's gum health. It is possible for the first and second steps as mentioned in the foregoing to be followed by a further step that involves determination whether or not the discrimination value is a value indicative of the presence of blood in a sample. Such a further step may particularly involve comparing the discrimination value to a reference value representing a predetermined limit value of a range of values indicative of the presence of blood in a sample. For the purpose of informing a user, it may be advantageous if a warning signal is emitted in case the discrimination value is found to be a value indicative of the presence of blood in a sample. To that end, the system according to the invention may be equipped with any suitable type of indicator.

The analysis unit of the system according to the invention is configured to perform at least the first and second steps. Hence, output of the analysis unit may come in the form of the discrimination value. It is also possible that the analysis unit is configured to perform the further step, in which case output of the analysis unit may come in a form that does not require further interpretation but is a direct indication as to whether or not blood is present in a sample and/or whether or not oral health issues may be assumed.

The background of the analysis steps is further explained as follows. The invention is concerned with providing a practical way of detecting blood traces in a sample of saliva or a sample of a fluid-saliva mix. For the purpose of indicating the likelihood that a person suffers from gingivitis or another condition affecting gum health, it is sufficient to detect whether or not blood is present in a sample. Thus, an important aspect of the invention is providing a way to discriminate blood against the background, which background may be one or more of saliva, water, toothpaste, mouthwash, etc.

It is known that the hemoglobin of blood has a light absorption spectrum in which absorption peaks can clearly be distinguished at wavelength values in a range of about 400-440 nm. For wavelength values of about 440 nm or higher, the absorption of hemoglobin is significantly lower. This is true for both oxyhemoglobin, i.e. hemoglobin with bound oxygen, and deoxygenated hemoglobin, i.e. hemoglobin without bound oxygen. Hence, for the purpose of determining whether or not a sample contains blood, it is advantageous if an optical measurement result is considered at a wavelength in the range of about 400-440 nm. Besides the optical measurement result at such a main wavelength, at least one other optical measurement result needs to be used for making an adjustment, i.e. a correction, namely for compensating for background influences, which can be done by using an optical measurement result at an auxiliary wavelength outside of the 400-440 nm range.

In tests performed in the context of the invention, it was found that it is actually possible to measure different corrected transmission values for a sample containing toothpaste and water but no blood on the one hand and a sample containing toothpaste and water and only a small amount of blood on the other hand. The particulars of those tests will be explained further in the detailed description of embodiments with reference to FIGS. 2 and 3.

It follows from the foregoing that for the purpose of providing an indication of a person's gum health, it is advantageous if hemoglobin is taken as the constituent of blood in the analysis to be performed, and if the main wavelength(s) is/are (a) wavelength(s) at which the light absorption of hemoglobin is relatively high and the auxiliary wavelength(s) is/are (a) wavelength(s) at which the light absorption of hemoglobin is relatively low. A main wavelength may be in a range of 410-430 nm, and an auxiliary wavelength may be 440 nm or higher. For example, an auxiliary wavelength may be chosen from a range of 440-470 nm. In a case in which measurement values of light relating to two main wavelengths are used in the analysis, a first main wavelength may be in the range of 410-430 nm as mentioned, while a second main wavelength may be in a range of 520-580 nm.

In many feasible situations, it may be sufficient to base an analysis on measurements results associated with two respective wavelengths, i.e. a main wavelength and one auxiliary wavelength. The use of a second auxiliary wavelength with a main wavelength may be useful if using one auxiliary wavelength is not sufficient to discriminate the blood against the background, which may be the case when a sample contains colored toothpaste and/or residues of food items and/or drinks, for example.

A notable advantage of the invention resides in the fact that there is no need for performing complex actions or using sophisticated and expensive equipment for performing the analysis of a sample containing saliva. In the first place, all that is needed for obtaining a sample that is suitable for investigation is performing a normal oral care action. Collecting the sample can be done in various ways, ranging from having an area on an oral care appliance that is particularly shaped for this purpose to having a person spit out some saliva. Further, commonly available light sources such as LEDs may be used as light-emitting units, possibly in combination with optical filters, and commonly available light detectors such as photodiodes may be used as light-receiving units, wherein there is no need for an expensive spectrometer. The analysis unit may be provided in the form of a preprogrammed microprocessor or a general microprocessor in combination with a suitable app or the like for controlling operation of the microprocessor, to mention two practical examples.

As mentioned in the foregoing, in a second step of the analysis, a discrimination value is determined that is suitable to be used for the purpose of determining whether or not an indication of the presence of blood in a sample is obtained. Within the scope of the invention, various possibilities exist when it comes to determination of a discrimination value. Examples of suitable ways of determining a discrimination value are the following:

- subtracting a measurement value relating to an auxiliary wavelength from a measurement value relating to a main wavelength,
- dividing a measurement value relating to a main wavelength by a measurement value relating to an auxiliary wavelength,
- dividing a difference value of a measurement value relating to an auxiliary wavelength and a measurement value relating to a main wavelength by a difference value of the wavelengths, and
- dividing a difference value of a measurement value relating to an auxiliary wavelength and a measurement value relating to a main wavelength by an addition value of the measurement values.

In respect of the first example of the way in which a discrimination value may be determined, it is noted that the respective measurement values may be transmission values, and that in the possible further step of the analysis, the discrimination value may be compared to a predetermined transmission value difference that is chosen so as to distinguish between a presence of blood and an absence of blood. When the discrimination value is higher than the predetermined transmission value difference, a presence of blood can be assumed, whereas when the discrimination value is lower than the predetermined transmission value difference, an absence of blood can be assumed.

In respect of the second example of the way in which a discrimination value may be determined, it is noted that the respective measurement values may be transmission values, that the determination of the discrimination value is in fact normalization of the transmission value related to the main wavelength, and that in the possible further step of the analysis, the discrimination value may be compared to a predetermined normalized transmission value that is chosen so as to distinguish between a presence of blood and an absence of blood. When the discrimination value is higher than the predetermined transmission value difference, an absence of blood can be assumed, whereas when the discrimination value is lower than the predetermined transmission value difference, a presence of blood can be assumed.

In respect of the third example of the way in which a discrimination value may be determined, it is noted that the respective measurement values may be transmission values, that the determination of the discrimination value is in fact a determination of a gradient of a slope of a graph plotting a transmission value against a wavelength, and that in the possible further step of the analysis, the discrimination value may be compared to a predetermined slope gradient that is chosen so as to distinguish between a presence of blood and an absence of blood. When the discrimination value is higher than the predetermined slope gradient, a presence of blood can be assumed, whereas when the discrimination value is lower than the predetermined slope gradient, an absence of blood can be assumed.

In respect of the fourth example of the way in which a discrimination value may be determined, it is noted that the respective measurement values may be transmission values, that the determination of the discrimination value is in fact a normalization of a transmission value difference to a transmission value total, and that in the possible further step of the analysis, the discrimination value may be compared to a predetermined ratio that is chosen so as to distinguish between a presence of blood and an absence of blood. When the discrimination value is higher than the predetermined ratio, a presence of blood can be assumed, whereas when the discrimination value is lower than the predetermined ratio, an absence of blood can be assumed.

As explained earlier, a notable aspect of the invention is the fact that processing measurements values relating to only a limited number of main wavelengths and a limited number of auxiliary wavelengths, probably no more than one or two main wavelengths and no more than one or two auxiliary wavelengths, is considered to be sufficient for discriminating blood (actually, the hemoglobin of the blood or possibly another constituent of the blood) against a background and thereby determining whether or not a sample contains blood. In view thereof, two of the possibilities existing in respect of the system according to the invention are the following:

- the light-emitting unit is configured to emit light at only the main wavelengths and the auxiliary wavelength(s), in which case it may be practical for the light-emitting unit to comprise two or more LEDs, part of the LEDs being configured to emit light at the main wavelength(s) and another part of the LEDs being configured to emit light at the auxiliary wavelength(s), and
- the light-receiving unit comprises two or more bandpass filter/light detector combinations, the bandpass filter of one or more bandpass filter/light detector combination being configured to only allow light at the main wavelength(s) to pass and the bandpass filter of one or more other bandpass filter/light detector combinations being configured to only allow light at the auxiliary wavelength(s) to pass.

The possibilities as mentioned are based on the insight that if measurement values related to only a limited number of wavelengths need to be analyzed, it may be sufficient to generate only such measurement values and no more. An advantage of generating only the measurement values needed for the analysis is that cheap and commonly available components may be applied.

In a practical embodiment, the system according to the invention may be equipped with an indicator configured to emit a signal in case the discrimination value is found to be in the range of values indicative of the presence of blood in a sample, i.e. above or below a reference value, whatever the case may be. The signal may be a visible signal and/or an audible signal, for example. In a general sense, the system according to the invention may be equipped with an output interface configured to communicate the information about gum health in a person's mouth, as determined and output by the analysis unit, to a user of the output interface, who may be the person herself/himself and/or another person such as a dentist. Outputting the information may be done through an app on the user's phone, for example, or on a suitable display. The output interface is adapted to generate output in a humanly processable form, i.e. in a form that can be detected by at least one of the human senses and processed in the human brain so as to make a human aware of the output of the output interface. Practical examples of output in a humanly processable form include output as can be detected by human vision, output as can be detected by human hearing and tactile output. In respect of the latter example, it is noted that when the invention involves use of an oral care appliance such as a power toothbrush, tactile output may be provided by varying the frequency and/or the amplitude of the motion of the functional unit (head) thereof. The analysis unit may be configured to transmit an information signal as a wireless signal, wherein there is no need for the analysis unit and the output interface to be physically connected in any way. The internet may be used for conveying the information signal to any person to whom the information generated by the analysis unit may be of interest. The results of successive analysis actions may be saved and may be subjected to further analysis so as to perform an assessment of trends over time.

Various known devices and objects may be adjusted so as to be capable of putting to the invention to practice and to thereby provide an indication of a person's gum health. For example, an assembly of the system according to the invention and a mobile device comprising a light, an image chip and a processor is feasible, wherein the analysis unit of the system comprises the processor of the mobile device, and wherein the at least one algorithm to be executed by the analysis unit is defined by an app installed on the mobile device. The mobile device may also comprise a light and an image chip, in which case it may be advantageous if the light-emitting unit of the system comprises the light of the mobile device and the light-receiving unit of the system comprises the image chip of the mobile device. Other configurations are possible, such as a configuration in which an app by means of which the at least one algorithm is defined is not installed on the mobile device but on a remote server that is accessible by the mobile device, or a configuration in which the analysis unit is arranged outside of the mobile device, in which case the mobile device can be provided with an app that is designed to let the mobile device transmit measurement data to the analysis unit.

According to another possibility of putting the invention to practice, an assembly of the system according to the invention and one of the bottom of a drinking glass, a cradle for holding a drinking glass, and an oral care appliance is provided, wherein at least the light-emitting unit and the light-receiving unit of the system are incorporated in the one of the bottom of the drinking glass, the cradle for holding a drinking glass, and the oral care appliance. In the case of the drinking glass, collecting the sample is done simply by letting the person under investigation spit some saliva in the drinking glass. In the case of the oral care appliance, it may be so that the oral care appliance is configured to be used in both a process of performing an oral care action which leads to the release of blood from the gums in case of reduced or poor gum health, and a process of determining whether or not blood is present in a sample containing saliva collected during the oral care action or right after the oral care action has taken place. In the first case, it is possible to obtain a real-time gum health indication during use of the oral care appliance, and also to obtain a range of localized indications in respect of various locations in a person's mouth if measures are taken for keeping track of a position of (a part of) the oral care appliance with respect to the person's mouth. The analysis unit may be provided outside of the oral care appliance, in which case it is advantageous if the oral care appliance is equipped with at least one unit that is designed to communicate with the analysis unit in a wireless fashion and/or another appropriate fashion.

It may be advantageous for an oral care appliance that is designed for use with the system according to the invention to comprise an area for accommodating a sample containing a person's saliva realized as a recess in the oral care appliance. This provides a possibility of taking and evaluating the sample containing the person's saliva in the person's mouth, which is an optimal way of obtaining an indication whether or not a person may suffer from reduced or poor gum health during an oral care routine performed on a regular basis.

The above-described and other aspects of the invention will be apparent from and elucidated with reference to the following detailed description of aspects of the theoretical background of the invention and a number of practical ways of putting the invention to practice.

BRIEF DESCRIPTION OF THE DRAWINGS

The invention will now be explained in greater detail with reference to the figures, in which equal or similar parts are indicated by the same reference signs, and in which.

DETAILED DESCRIPTION OF THE EMBODIMENTS

The invention provides a practical way of providing an indication of a person's gum health. According to the invention, the presence of blood traces in a sample containing a person's saliva is evaluated by performing optical measurements and analyzing the results of the measurements, wherein an appropriate choice is made when it comes to the wavelengths of measurement values which are considered in the process.

The invention is particularly aimed at providing a way of detecting blood traces in saliva or a toothpaste-saliva mix for the purpose of obtaining an indication that the person whose saliva is under investigation may suffer from (early stage) gingivitis or from another condition affecting gum health. In view thereof, the invention provides a reliable method for detecting low hemoglobin concentrations, by using optical detection based on the known absorption peaks in the hemoglobin absorption spectrum. As is generally known, hemoglobin is an important constituent of blood.

Figure 1:
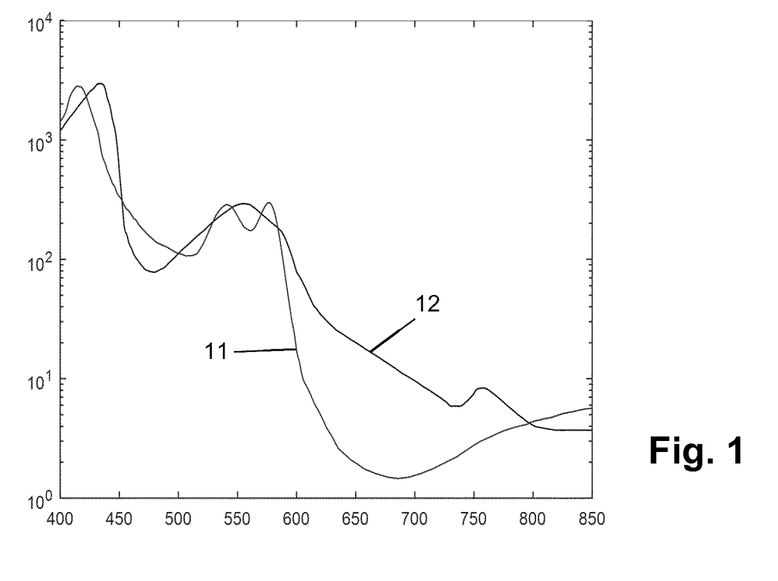
FIG. 1 shows absorption spectra of hemoglobin.

FIG. 1 shows two absorption spectra of hemoglobin, wherein the spectrum that is indicated by reference numeral 11 is related to oxyhemoglobin, i.e. hemoglobin with bound oxygen, and wherein the spectrum that is indicated by reference numeral 12 is related to deoxygenated hemoglobin, i.e. hemoglobin without bound oxygen. The wavelength of light expressed in nm is at the x axis of the spectra, and the absorption coefficient expressed in $cm^{-1}$ is at the y axis of the spectra. It appears from the figure that there are some specific, highly absorbing wavelength ranges. Especially the blue wavelength range of 410-430 nm involves relatively high values of the absorption coefficient of the hemoglobin.

In the context of the invention, it is sufficient to check whether or not blood is present in a sample containing saliva, wherein there is no need for determining the concentration of the blood in the sample. The invention provides a way of discriminating blood against a background of saliva or a mix of saliva and toothpaste in order to check a sample containing saliva, obtained during or after an oral care action such as brushing or flossing for traces of blood. It is known that in the wavelength range of 410-430 nm as mentioned, the absorption coefficient of water is relatively low. As water is the main constituent of saliva, there is no need to take the saliva factor into account. However, the absorption characteristics of toothpaste may be expected to constitute a factor that necessitates a correction of measurement values obtained in the wavelength range of 410-430 nm.

Figure 2:
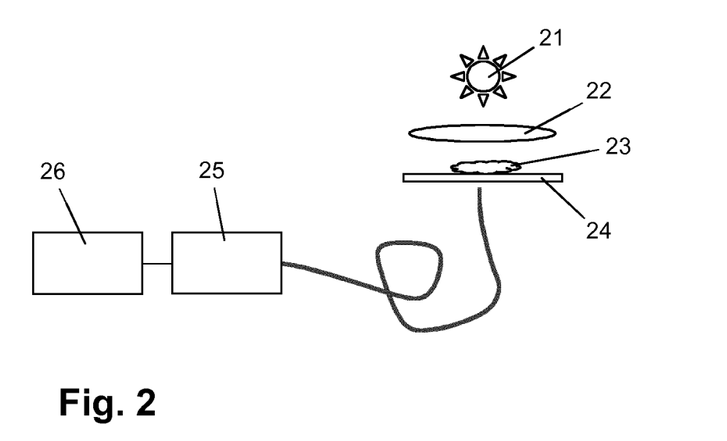
FIG. 2 illustrates the setup of a test arrangement for detecting a presence of blood in a toothpaste-saliva mix.

To investigate the feasibility of discriminating blood against a background of toothpaste, tests were performed, using a test arrangement of which the setup is illustrated in FIG. 2. FIG. 2 diagrammatically shows a light source 21, a collimator 22, a sample 23 to be investigated as present on a glass slide 24, and a light detector 25 coupled to an analysis unit 26. Toothpaste and water were mixed in a 1:5 ratio after which small amounts of human blood were added to the mix. A dilution series of up to 10,000 times more toothpaste and water than blood was made to test whether the presence of blood could be found even in extremely small concentrations, comparable to the presence of a tiny drop of blood of about 0.5 μl in 5 ml of toothpaste-saliva mix. The volume of 5 ml of toothpaste-saliva mix can be regarded as an example of a volume a person ends up with in her/his mouth after a brushing action. The 10,000 dilution can be regarded as being representative of a worst case scenario as 0.5 μl is an extremely small drop and a person will normally lose more blood from bleeding gums, especially if more than one spot in the mouth is bleeding due to an oral care action.

Figure 3:
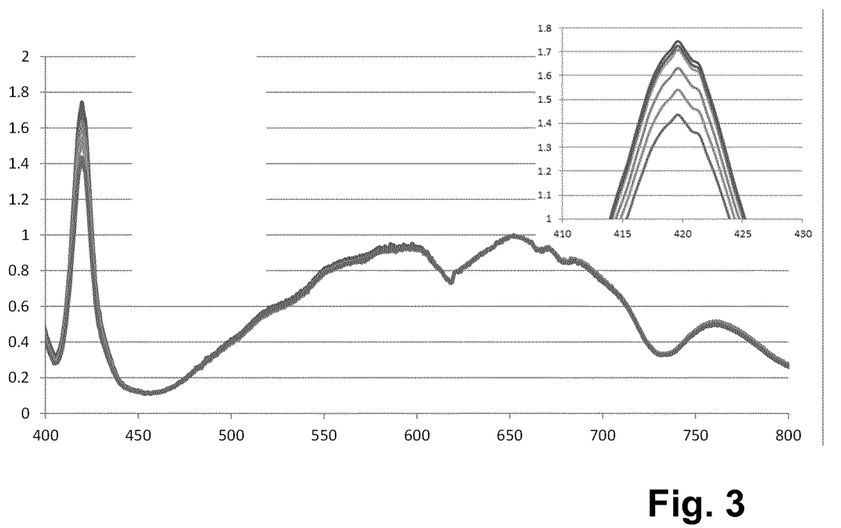
FIG. 3 shows normalized transmission spectra of toothpaste solutions with various hemoglobin concentrations.

FIG. 3 provides an illustration of the results of transmission measurements for a mix of saliva and a particular type of toothpaste. The figure shows transmission spectra for a sample without blood and five different dilutions, all normalized to a wavelength of 650 nm, which is a wavelength where the blood contribution, i.e. the absorption of light by blood (hemoglobin), may be expected to be low. The wavelength of light expressed in nm is at the x axis of the spectra, and the normalized transmission, i.e. the range of transmission values relating to a particular dilution divided by the transmission value related to that particular dilution at the 650 nm wavelength, is at the y axis of the spectra. The five different dilutions are dilutions of 1:10,000; 1:1,000; 1:500; 1:100 and 1:50, respectively.

The insert of FIG. 3 shows an enlargement of the peak values of the normalized transmission, particularly the values of 1 and higher. The top graph is related to the sample that does not contain any blood. In the peak area, which is typically associated with wavelengths in a range of 410-430 nm, all normalized transmission values related to the other samples are lower than the normalized transmission values related to the sample without blood. The normalized transmission value of the 1:10,000 dilution appears to represent a drop in transmission of about 2% with respect to the normalized transmission value of the dilution without blood. This means that the presence or absence of blood can be determined in a sample containing saliva, indeed.

It follows from the tests that were performed that it is very well possible to detect the presence of blood (hemoglobin) in a mix of saliva and toothpaste, particularly to discriminate blood against toothpaste. At the higher wavelength values, the transmission values are mainly influenced by the presence of toothpaste while the blood absorption is very low, whereas at the lower wavelength values, especially the values in the range of 410-430 nm, the contribution of the blood is far more significant. In case a particular type of toothpaste has a color on the basis of which the toothpaste is highly absorbing in the same range of wavelengths as blood, a third measurement value obtained at a third wavelength can be used for further correction. It follows from FIG. 1 that a huge drop in light absorption by blood is present at wavelengths which are only a little bit higher than the wavelength range of 410-430 nm. It is very unlikely that toothpaste exists which has exactly the same characteristics. Therefore, investigating the characteristics in the wavelength area where the large drop of measurement values associated with blood may be expected is useful when it comes to discriminating blood against toothpaste. Alternatively, a calibration step may be performed prior to the measurements, using water and toothpaste only, in which case there is no need for using the transmission values from more than two wavelengths.

All in all, it follows from the tests that even a simple setup is sufficient for enabling detection of small amount of blood in a solution containing toothpaste. The invention provides a way of detecting much lower blood concentrations in a toothpaste-saliva mix than can be done by the human eye, and therefore enables detection of gingivitis or other conditions affecting gum health in an early, reversible stage. The detection can be done with as little influence on normal oral care routines as possible. For example, when the invention is realized in an oral care appliance as will be explained later, it is even possible that a sample containing saliva is taken automatically and is subjected automatically to optical analysis.

It is noted that besides measuring spectral transmission through a solution, it is also possible to measure diffuse reflectance properties of a solution. This is advantageous because performing reflectance measurements allows for obtaining an indication of a person's gum health from a sample containing saliva that is present on a non-transparent carrier such as a sink surface. In such a case, a person who is to be investigated only needs to spit out saliva in the sink at some time during an oral care action, or shortly after the oral care action has taken place. The measurement of light absorption/transmission values and the processing of those values related to two or more predetermined wavelengths of the light can take place by means of a tool having a basic setup as illustrated in FIG. 2, for example, wherein the light detector 25 is placed at the same side of the glass slide 24 with the sample 23 as the light source 21 and the collimator 22 so as to allow for performing measurements of light in reflection. Such a tool may be a tool that is especially designed for that purpose, but may also be a smartphone, for example, as will be explained later in the present text, in which case enhancement of the sensitivity can be achieved by performing a baseline measurement, i.e. by first measuring the characteristics of a clean background without saliva/toothpaste on it.

In the following, a number of preferred ways in which the invention may be put to practice are explained. The first two options relate to a diffuse reflective setup of the arrangement for obtaining measurement results suitable for use in assessing a person's gum health, which, as follows from the foregoing, involves the advantage of not requiring a separate container for receiving the sample containing saliva, which does not alter the fact that it is possible to use one.

Figure 4:
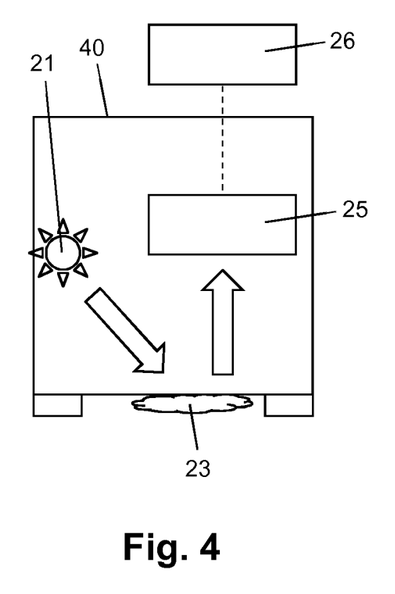
FIG. 4 illustrates how the invention may be realized in a diffuse reflective probe.

According to a first option existing within the framework of the invention, a diffuse reflective probe 40 as illustrated in FIG. 4 is provided, including an illumination spot coupled to a light source 21, for illumination of a sample 23 to be analyzed. Preferably, the light source 21 is modulated to reject ambient light. The diffuse reflective probe 40 further includes a light detector 25 coupled to an analysis unit 26 configured to determine whether or not blood is present in the sample 23 and to provide an indication that it is likely that a person suffers from reduced or poor gum health, or not. In the figure, paths of the emitted light and the reflected light are indicated by means of arrows. In a spectral detection process, two wavelengths are covered: one main wavelength for measuring the absorption of hemoglobin, preferably chosen from a range of 410-430 nm, and one auxiliary wavelength chosen from a range where the absorption of hemoglobin is known to be considerably less, such as a wavelength in a range of 440-470 nm or a wavelength higher than 650 nm. As one step in the analysis, a correction of the reflection values is done, which may be normalization of the main wavelength reflection with the auxiliary wavelength reflection. In that way, a discrimination value is obtained, that is evaluated in order to see whether the measurement supports a presence of blood in the sample 23. The probe 40 may be equipped with a suitable indicator for issuing a warning signal in case blood appears to be detected.

The light detector 25 can be realized in various suitable ways. For example, the light detector 25 may comprise two bandpass filter/detector combinations. Further, the light source 21 can comprise an incandescent lamp or a broadband LED such as a phosphor converted white or amber LED. In such a case, the blue pump light provides the light at the main wavelength while the phosphor converted LED provides the light at the auxiliary wavelength. An alternative is to use one detector such as a photodiode and two different LEDs, wherein one LED emits light at the main wavelength while the other LED emits light at the auxiliary wavelength. The two LEDs can be used in a time-sequential mode, or simultaneously using different modulations of the LEDs. Increased sensitivity can be achieved by supplying each of the LEDs with a narrowband bandpass filter.

In respect of a possible use of LEDs, it is further noted that blue wavelengths of white lighting LEDs normally have a value of about 440 nm and may have a FWHM (full width at half maximum) of 30 nm. In order to still be able to perform an analysis based on a main wavelength in a range just below 440 nm and an auxiliary wavelength in a range just above 440 nm in case such white lighting LEDs are used, it is a feasible possibility to modulate the LEDs so that measurement light may be discriminated against the blue wavelengths of the lighting LEDs.

According to a second option existing within the framework of the invention, a smartphone or other mobile device is used to take an image of toothpaste-saliva remains on a sink surface or the like. In such a case, the auxiliary wavelength can be taken from the red or the green channel from the image chip of the smartphone, wherein it is noted that taking the auxiliary wavelength from the red channel is preferred. Since the camera of a smartphone has the possibility/tendency to acquire the specular reflection, it is advantageous to supply the smartphone with a cross polarizer foil. This is a practical way of ensuring that only diffuse reflective images, which contain the spectral characteristics required for performing the analysis as envisaged, are taken. Another (possibly additional) setup that can be used to increase sensitivity involves applying a multiple passband optical filter. It is preferred for such a filter to only transmit light at the main wavelength and the auxiliary wavelength and to be held in an add-on that is designed for placement over the (flash) LED and the camera lens of the smartphone. An additional benefit of using such a filter is the fact that ambient light is largely eliminated in that way.

According to a third option existing within the framework of the invention, the transmissive setup is used. An advantage of the transmissive setup is higher sensitivity. A disadvantage of the transmissive setup is the requirement of a container/carrier to collect the sample containing saliva. The basic setup in this case can be as illustrated in FIG. 2. The glass slide 24 shown in the figure can be replaced by a (disposable) plastic slide having a depression for containing the sample 23. The plastic slide can be inserted in a measurement and analysis device including a light source 21, a light detector 25 and an analysis unit 26 for performing the blood detection. For the sake of completeness, it is noted that the alternatives for the light detector 25 and the light source 21 mentioned in respect of the first option are equally applicable to the present third option.

The plastic slide may come in various embodiments. It is possible for the slide to be provided with at least one capillary channel to transport saliva to at least one chamber of the slide. This allows for cleaning the slide prior to placement of the slide in a measurement and analysis device. Alternatively, it may be so that only the part of the slide having the at least one chamber is placed in the device, wherein a messy part of the slide covered in saliva is allowed to project from the device, so that a cleaning action is not necessary.

Figure 5:
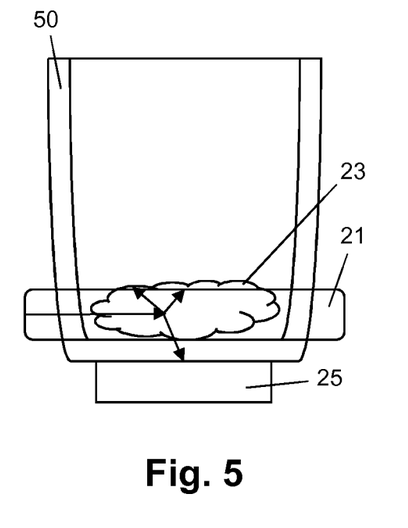
FIG. 5 illustrates how the invention may be realized in a drinking glass.

According to a fourth option existing within the framework of the invention, a simple drinking glass 50 is equipped with a light source 21 and a light detector 25 near the bottom of the glass 50, as illustrated in FIG. 5. For the purpose of having a toothpaste-saliva sample 23 analyzed, a person spits toothpaste-saliva foam in the glass 50. Light that enters through the glass 50 from a light source 21 arranged around the glass 50 is scattered in the foam towards the light detector 25, as indicated by arrows in the figure. In a variation, a separate cradle for receiving and supporting a drinking glass 50 is used, wherein a light source 21 and a light detector 25 are integrated in the cradle.

Figure 6:
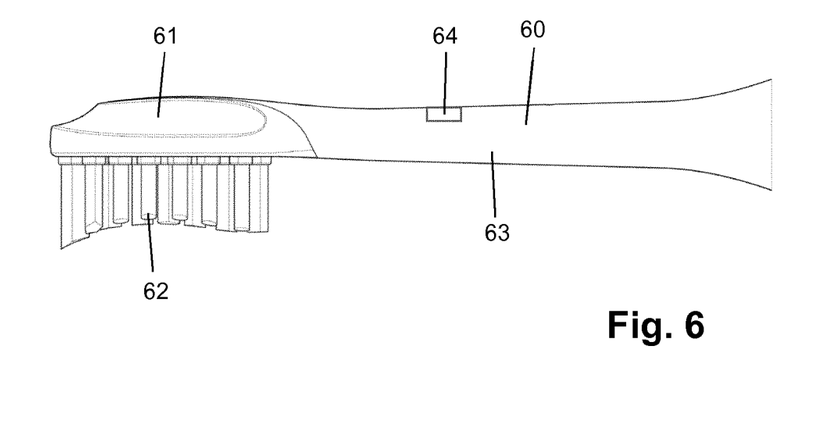
FIGS. 6-8 illustrate how the invention may be realized in an oral care appliance.
Figure 7:
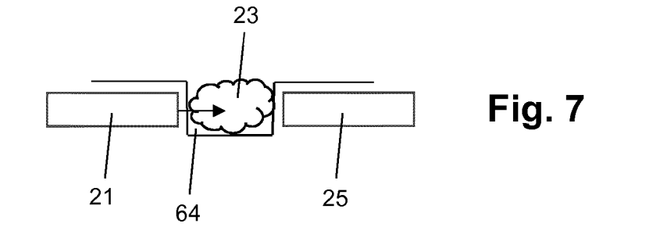
Figure 8:
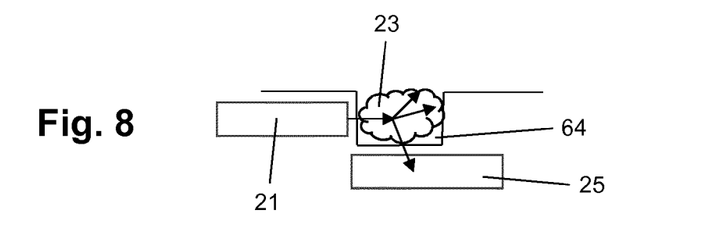

According to a fifth option existing within the framework of the invention, an oral care device is configured to perform one or more functions in a process of detecting blood traces in a sample containing saliva. An example of this option is illustrated in FIGS. 6-8. In FIG. 6, a brush head part 60 of a power toothbrush is shown. In the context of a power toothbrush, toothpaste-saliva foam will collect automatically on the brush head 61 between the tufts 62 during operation of the power toothbrush. In view thereof, it may be advantageous to have an optical window at the position of the tufts 62 in the brush head 61, and also to have a light source and a light detector arranged in the brush head 61, so that a reflection measurement can be performed. The toothpaste-saliva foam will also collect automatically on the backside of the brush head 61. It may therefore also be practical if an optical window is provided in the backside of the brush head 61. According to yet another possibility, the neck portion 63 of the brush head part 60 may be provided with a recess 64 for the purpose of collecting toothpaste-saliva foam during a brushing action. Such a recess 64 may be used for detecting a presence of blood traces through transmission measurement, as illustrated in FIG. 7, which is the case when the light detector 25 is arranged in a light path from the light source 21 and is at a position for receiving light traveling through the toothpaste-saliva foam 23, or through reflection measurement, as illustrated in FIG. 8, which is the case when the light detector 25 is arranged outside of a light path from the light source 21 and is at a position for receiving light reflected by the toothpaste-saliva foam 23 instead.

In general, the invention covers the possibility that an oral care device has an optical window at an appropriate position on the device, such as on a functional head of the device or on a neck portion or body portion, and a light-emitting unit and a light-receiving unit associated with the optical window. It is practical for the optical window to be arranged at a position of an area where saliva accumulates during use of the oral care device, which may be the position of a recess, as explained.

In the case of an oral care device, it is possible to keep track of a position of (a part of) the oral care device with respect to the mouth. For example, if a toothbrush is used, information about the actual position of the brush head 61 may continually be available on the basis of suitable control and/or detection measures. In the context of the invention, such information may be used for obtaining gum health indications at a local level, so that areas of reduced/poor gum health in the mouth may be distinguished from areas of acceptable/good gum health. In this respect, it is noted that it may be advantageous to monitor time dependence of the reflection during an oral care action, assuming that a slow and continuous lowering of the reflection signal means dilution, and that a sudden and fast lowering of the signal means (additional) optical absorption caused by release of blood. Thus, by monitoring time dependence of the signal that is obtained from the oral care device, it is possible to keep track of moments at which a release of blood is invoked. In combination with positioning information, this may help in finding "hot spots" in the mouth, i.e. areas which are made to bleed easily and which may be assumed to have poor gum health.

In the context of toothbrushes and other oral care devices, it is possible that a cradle of the device is provided, and that an analysis unit 26 and an associated output interface are incorporated in the cradle. An oral care device does not necessarily need to have an optical window and an associated light source 21 and light detector 25 arranged in a part of the device that is destined to be put into a person's mouth during use of the device. The fact is that it is also possible that an oral care device is equipped with components as mentioned at a bottom of a handle thereof, in which case the device is suitable to be used for detecting spectral characteristics of a saliva sample that has been spit on a surface.

Designing an oral care device for putting the invention to practice involves the advantage that the detection of blood traces for the purpose of assessing a person's gum health can be performed automatically during an oral care action, or requires only minimum additional effort without the need for additional tools.

It will be clear to a person skilled in the art that the scope of the invention is not limited to the examples discussed in the foregoing, but that several amendments and modifications thereof are possible without deviating from the scope of the invention as defined in the attached claims. It is intended that the invention be construed as including all such amendments and modifications insofar they come within the scope of the claims or the equivalents thereof. While the invention has been illustrated and described in detail in the figures and the description, such illustration and description are to be considered illustrative or exemplary only, and not restrictive. The invention is not limited to the disclosed embodiments. The drawings are schematic, wherein details which are not required for understanding the invention may have been omitted, and not necessarily to scale.

Variations to the disclosed embodiments can be understood and effected by a person skilled in the art in practicing the claimed invention, from a study of the figures, the description and the attached claims. In the claims, the word "comprising" does not exclude other steps or elements, and the indefinite article "a" or "an" does not exclude a plurality. Any reference signs in the claims should not be construed as limiting the scope of the invention.

Elements and aspects discussed for or in relation with a particular embodiment may be suitably combined with elements and aspects of other embodiments, unless explicitly stated otherwise. Thus, the mere fact that certain measures are recited in mutually different dependent claims does not indicate that a combination of these measures cannot be used to advantage.

The term "comprise" as used in this text will be understood by a person skilled in the art as covering the term "consist of". Hence, the term "comprise" may in respect of an embodiment mean "consist of", but may in another embodiment mean "contain/include at least the defined species and optionally one or more other species".

For the sake of clarity and correct interpretation of the present text including the claims, it is noted that where a specific wavelength value is mentioned in relation to a device such as a light source or a filter, this is to be understood for its practical meaning rather than its theoretical meaning, taking into account that in fact a tolerance window is applicable.

As known from the art, in the context of absorption spectroscopy, absorption and transmission spectra represent similar information and one can be calculated from the other. Peaks of a transmission spectrum are present at wavelengths where absorption is at a minimum, and peaks of an absorption spectrum are present at wavelengths where transmission is at a minimum.

In the present text, denoting light absorption as higher or relatively high on the one hand and as lower or relatively low on the other hand implies that the one light absorption is notably higher than the other light absorption. With reference to an absorption spectrum, higher or relatively high light absorption is related to peaks of the spectrum, whereas lower or relatively low light absorption is not and is rather related to valleys of the spectrum.

A summary of the invention may read as follows. An optical analysis of saliva or a fluid-saliva mix obtained during or after an oral care action is performed in order to check whether the saliva or fluid-saliva mix contains blood, which allows for determining whether or not a person may suffer from gingivitis or another condition affecting gum health. In particular, light received from a representative sample containing saliva is detected and analyzed, which light is obtained by emitting light to the sample and receiving the light back from the sample. The analysis involves determination of measurement values of light received by a light-receiving unit for one or more main wavelengths (a limited number of main wavelengths) of the light, and also for one or more auxiliary wavelengths (a limited number of auxiliary wavelengths) of the light. Advantageously, the main wavelength(s) is/are associated with high hemoglobin absorption and the auxiliary wavelength(s) is/are associated with low hemoglobin absorption. A measurement value at an auxiliary wavelength is used for correcting a measurement value at a main wavelength for background influences.

The invention claimed is:
1. A device for providing an indication of gum health based on a presence of blood traces in saliva, comprising:
   a light-emitting unit configured to emit light to a sample containing saliva;
   a light-receiving unit configured to receive light reflected back from the sample; and
   an analysis unit configured to perform an analysis of the light received by the light-receiving unit and to provide output representative of gum health, and configured to:
      determine measurement values of light received by the light-receiving unit for one or more main wavelengths of the light related to higher light absorption by a constituent of blood, and for one or more auxiliary wavelengths of the light related to lower light absorption by the constituent of blood, and
      determine a discrimination value on the basis of the measurement values, wherein in the process of determining the discrimination value, a measurement value relating to the one or more main wavelengths is adjusted with one or more measurement values relating to the one or more of the auxiliary wavelengths so as to correct the measurement value relating to the one or more main wavelengths for background influences,
   wherein at least the light-emitting unit and the light-receiving unit are incorporated into an oral care appliance, and
   wherein the oral care appliance including a neck portion connected to a brush head, the brush head having tufts extending from a bottom surface thereof, wherein the light-emitting unit and the light-receiving unit are configured to emit and receive light through a first optical window in at least one of the bottom surface of the brush head and neck portion of the oral care appliance.

2. The device according to claim 1, wherein the discrimination value is determined by one of
   subtracting the one or more measurement values relating to the one or more auxiliary wavelengths from the measurement value relating to the one or more main wavelengths,
   dividing the measurement value relating to the one or more main wavelengths by the one or more measurement values relating to the one or more auxiliary wavelengths,
   dividing a difference value of the one or more measurement values relating to the one or more auxiliary wavelengths and the measurement value relating to the one or more main wavelengths by the difference value of the measurement values, and
   dividing the difference value of the one or more measurement values relating to the one or more auxiliary wavelengths and the measurement value relating to the one or more main wavelengths by an addition value of the measurement values.

3. The device according to claim 1, wherein the analysis unit executes a further step of determining whether the discrimination value is a value indicative of the presence of blood in the sample.

4. The device according to claim 1, wherein the one or more main wavelengths is a wavelength at which the light absorption of hemoglobin is higher relative to the light absorption of hemoglobin at the one or more auxiliary wavelengths.

5. The device according to claim 1, wherein at least one of the main wavelengths is in a range of 410-430 nm.

6. The device according to claim 1, wherein at least one of the auxiliary wavelengths is 440 nm or higher.

7. The device according to claim 1, wherein the light-emitting unit is configured to emit light at only the one or more main wavelengths and the one or more auxiliary wavelengths.

8. The device according to claim 1 wherein the analysis unit of the system comprises a mobile device.

9. The device according to claim 8, wherein the light-emitting unit comprises a light emitting unit in the mobile device, and wherein the light-receiving unit comprises an image chip of the mobile device.

10. The device according to claim 1, wherein the analysis unit is configured to perform the analysis of light received by the light-receiving unit during an oral care action performed by means of the oral care appliance.

11. The device according to claim 1 further comprising a bandpass filter configured to allow light from the light-emitting unit only at the one or more main wavelengths to pass.

12. The device according to claim 1 further comprising a bandpass filter configured to allow light from the light-emitting unit only at the one or more auxiliary wavelengths to pass.

13. The device according to claim 1, wherein the first optical window is located in a recess formed in the neck portion of the oral care appliance.

14. The device according to claim 1, further comprising a second optical window located in a top surface of the brush head of the oral care appliance.

15. A method of providing an indication of gum health on the basis of an evaluation of a presence of blood traces in a sample containing saliva, comprising the steps of:
   emitting light from a light-emitting unit of an oral care appliance to the sample containing the saliva;
   receiving light reflected back from the sample using a light receiving unit of the oral care appliance;
   determining measurement values of the light received back from the sample for one or more main wavelengths of the light related to higher light absorption by a constituent of blood, and for one or more auxiliary wavelengths of the light related to lower light absorption by the constituent of blood, and
   determining a discrimination value on the basis of the measurement values, wherein in the process of determining the discrimination value, a measurement value relating to the one or more main wavelengths is adjusted with a measurement value relating to the one or more auxiliary wavelengths so as to correct the measurement value relating to the one or more main wavelengths for background influences,
   wherein the oral care appliance including a neck portion connected to a brush head, the brush head having tufts extending from a bottom surface thereof, wherein the light is emitted and received through a first optical window in at least one of the brush head and neck portion of the oral care appliance.

16. The method according to claim 15, further comprising the step of determining whether the discrimination value is a value indicative of the presence of blood in the sample.

17. The method according to claim 16, wherein a warning signal is provided when the discrimination value is found to be the value indicative of the presence of blood in the sample.

18. The method according to claim 15, wherein the first optical window is located in a recess formed in the neck portion of the oral care appliance.

19. The method according to claim 15, further comprising emitting and receiving light through a second optical window located in a top surface of the brush head of the oral care appliance.

* * * * *